(12) United States Patent
Nickel et al.

(10) Patent No.: US 8,444,935 B2
(45) Date of Patent: May 21, 2013

(54) MULTIPLE-SPECIMEN DEVICE TESTING WITH PARTICLE MEASUREMENT

(75) Inventors: Troy D. Nickel, Minneapolis, MN (US); David Louis Dingmann, St. Paul, MN (US); Mark Hanson, St. Paul, MN (US)

(73) Assignee: Bose Corporation, Framingham, MA (US)

(*) Notice: Subject to any disclaimer, the term of this patent is extended or adjusted under 35 U.S.C. 154(b) by 630 days.

(21) Appl. No.: 12/483,533

(22) Filed: Jun. 12, 2009

(65) Prior Publication Data

US 2010/0313683 A1 Dec. 16, 2010

(51) Int. Cl.
 *B01L 3/02* (2006.01)
(52) U.S. Cl.
 USPC ........... 422/509; 422/505; 422/513; 422/518; 422/521; 422/527; 436/180
(58) Field of Classification Search
 USPC ......... 422/500, 505, 509, 513, 518, 521–522, 422/527, 534, 112, 63; 436/180
 See application file for complete search history.

(56) References Cited

U.S. PATENT DOCUMENTS

| | | | |
|---|---|---|---|
| 3,039,399 A | | 6/1962 | Everett |
| 3,958,938 A | * | 5/1976 | Doonan et al. ............... 435/30 |
| 4,294,800 A | * | 10/1981 | Tavlarides et al. ............ 422/50 |
| 5,149,659 A | * | 9/1992 | Hakuta et al. ................. 436/55 |
| 5,477,882 A | * | 12/1995 | Duthie ...................... 137/565.19 |
| 5,670,708 A | | 9/1997 | Vilendrer |
| 5,779,977 A | * | 7/1998 | Haff et al. .................... 422/68.1 |
| 5,827,480 A | * | 10/1998 | Haff et al. .................... 422/68.1 |
| 7,235,164 B2 | * | 6/2007 | Anex et al. ..................... 204/600 |
| 7,591,198 B2 | | 9/2009 | Weldon et al. |
| 7,591,199 B2 | | 9/2009 | Weldon et al. |
| 7,642,089 B2 | * | 1/2010 | Pieper et al. ............... 435/288.6 |
| 7,875,159 B2 | | 1/2011 | Anex et al. |
| 2003/0066338 A1 | | 4/2003 | Michalsky et al. |
| 2003/0170903 A1 | * | 9/2003 | Johnson et al. ............... 436/100 |
| 2004/0016301 A1 | | 1/2004 | Moreno et al. |
| 2007/0185534 A1 | | 8/2007 | Conti et al. |
| 2008/0295606 A1 | | 12/2008 | Chinavare |

(Continued)

FOREIGN PATENT DOCUMENTS

| | | |
|---|---|---|
| GB | 1256070 | 12/1971 |
| GB | 1256070 A | 12/1971 |

OTHER PUBLICATIONS

Conti, et al.; A Comprehensive Protocol and Procedural Considerations Designed to Evaluate the Shedding of Particles from Drug Eluting Stents, Presented at the Materials and Processes for Medical Devices Conference, Palm Desert, California (2007).

(Continued)

*Primary Examiner* — Brian R Gordon

(57) ABSTRACT

A sample testing system includes a plurality of sample tubes, each sample tube coupled to a pumping chamber, a pressure control subsystem and a flow control subsystem. The pressure control system includes a first dynamic pump equipped to induce pulsatile pressure in a mass of pumping fluid coupled to the pumping chambers. The flow control subsystem includes a mean flow pump equipped to generate a flow of sample fluid in a plurality of flow loops. Each of the flow loops conducts the flow of sample fluid between the mean flow pump and one of the sample tubes. The pumping chamber couples pressure from the pumping fluid to the sample fluid.

21 Claims, 10 Drawing Sheets

U.S. PATENT DOCUMENTS

2009/0000388 A1  1/2009  Nickel et al.
2009/0019950 A1  1/2009  Dingmann et al.
2012/0111888 A1*  5/2012  Smith .................. 222/129.1

OTHER PUBLICATIONS

International Search Report and Written Opinion for PCT/US2010/036633, dated Sep. 7, 2010, 13 pages.

Foy, Common Pitfalls in Drug Eluting Stent Applications, Town Hall Meeting with FDA at CRT., Jan. 29, 2003.

Vilendrer and Oktay, In Vitro Durability Testing of Coated Stents, Proceedings from the Materials & Processes for Medical Devices Conference, Sep. 8-10, 2003, Anaheim, Calif. ASM International, 2004, pp. 226-229.

Foy, Steps to a Successful DES development Program, FDA Regulatory Pathways Workshop at CRT, May 6, 2004.

Oktay, Drug Eluting Stents—Pre Clinical Testing Challenges, soktay@cardiomedlic.com Mar. 30, 2004.

Foy, Common Pitfalls in Drug Eluting Stent Applications, Town Hail Meeting with FDA at CRT., Jan. 29, 2003.

First Chinese Office Action dated Mar. 1, 2013 for Chinese Application No. 201080032620.3.

* cited by examiner

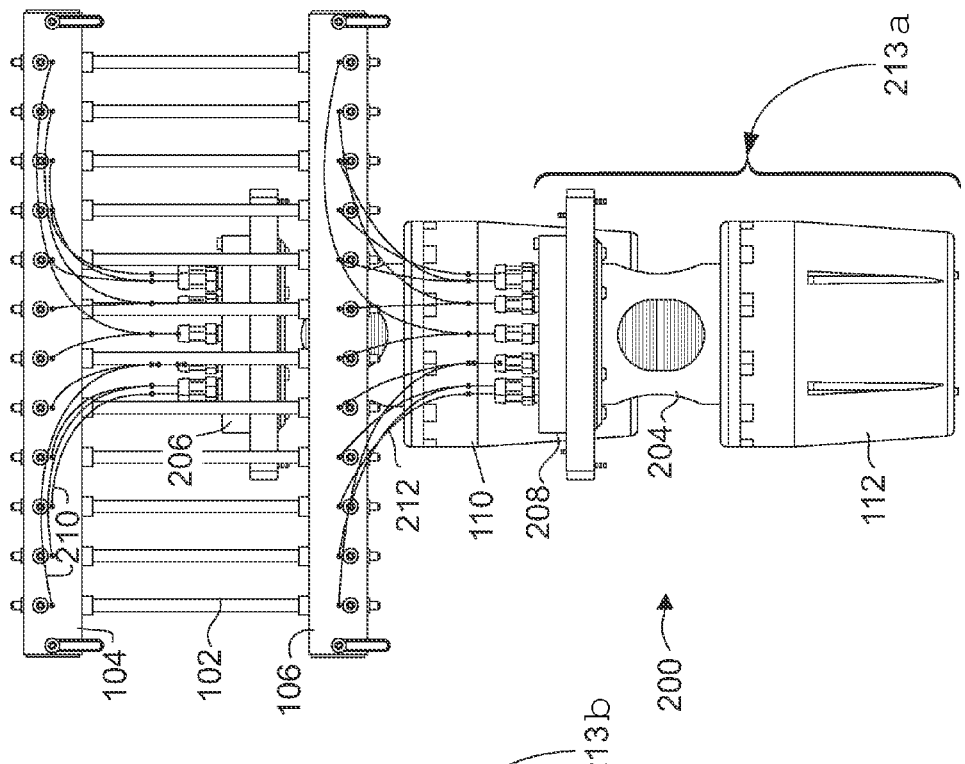
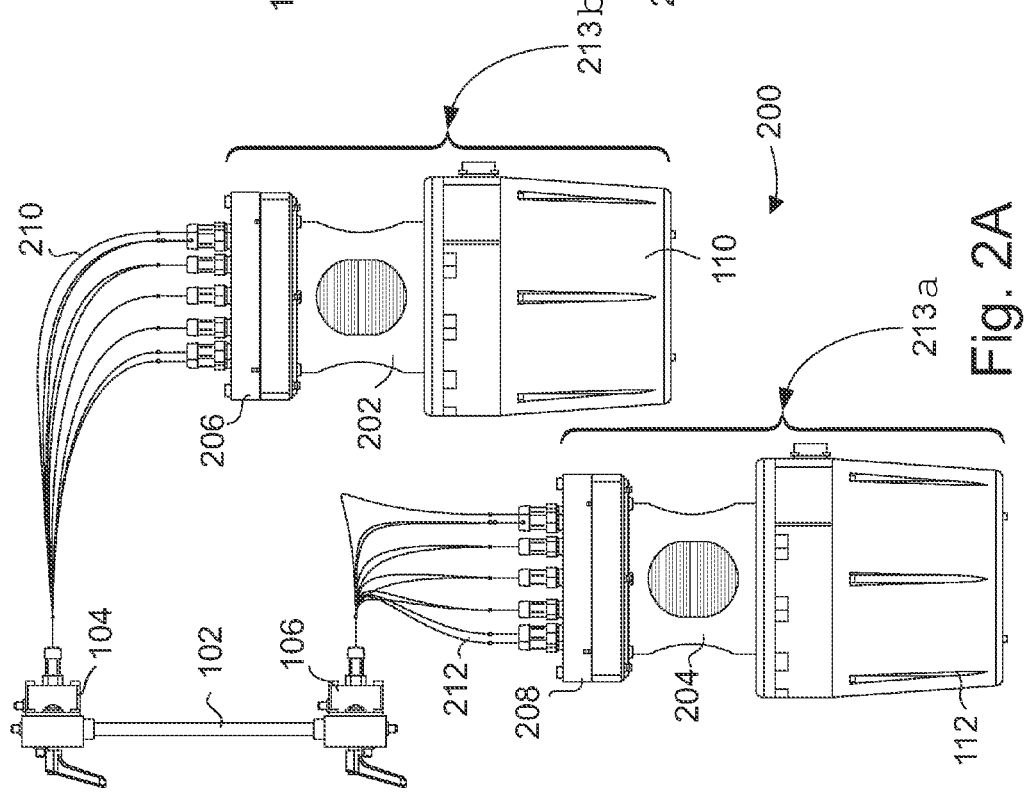

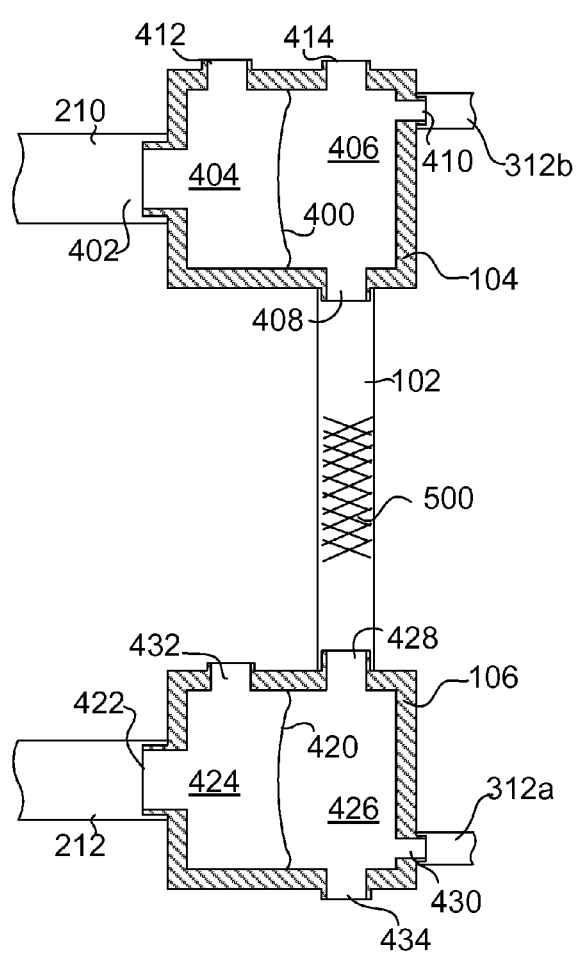
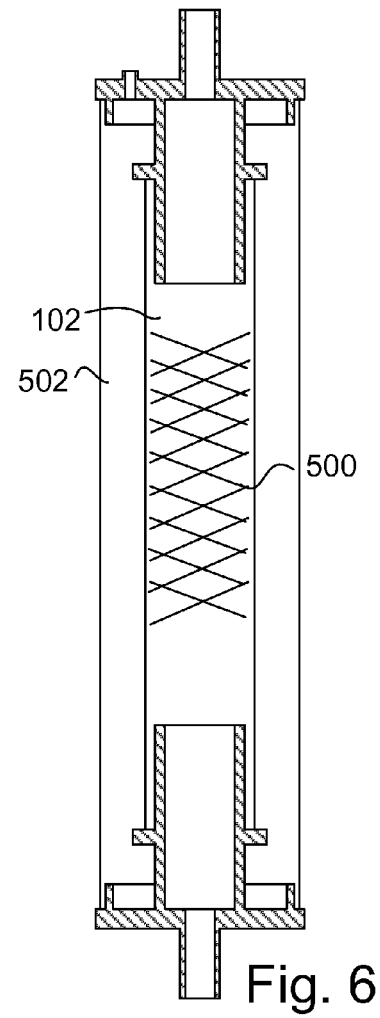
Fig. 5A
Fig. 6
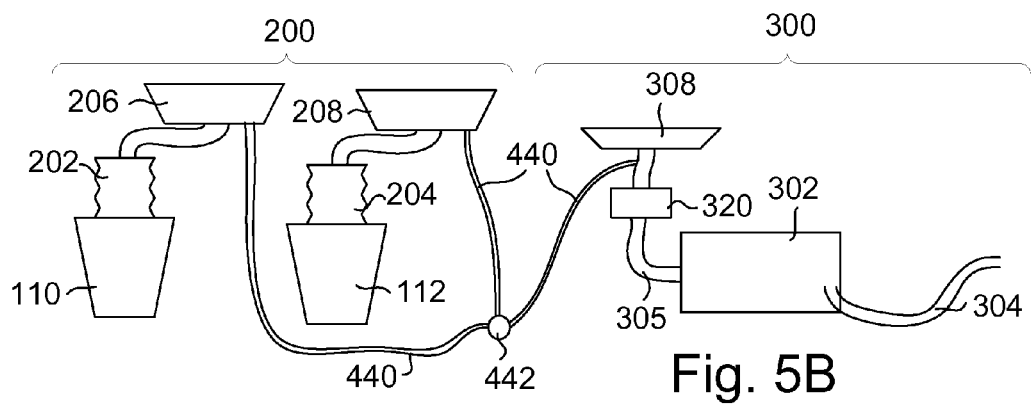
Fig. 5B

MULTIPLE-SPECIMEN DEVICE TESTING WITH PARTICLE MEASUREMENT

BACKGROUND

This disclosure relates to multiple-specimen device testing with particle measurement.

Equipment for simultaneously testing multiple implantable medical devices, such as stents or stent/grafts, is described in U.S. Pat. No. 5,670,708, incorporated here by reference.

SUMMARY

In general, in some aspects, a sample testing system includes a plurality of sample tubes, each sample tube coupled to a pumping chamber, a pressure control subsystem and a flow control subsystem. The pressure control system includes a first dynamic pump equipped to induce pulsatile pressure in a mass of pumping fluid coupled to the pumping chambers. The flow control subsystem includes a mean flow pump equipped to generate a flow of sample fluid in a plurality of flow loops. Each of the flow loops conducts the flow of sample fluid between the mean flow pump and one of the sample tubes. The pumping chamber couples pressure from the pumping fluid to the sample fluid.

Implementations may include one or more of the following features.

Each sample tube is coupled to the pumping chamber at a first end and is coupled to a second pumping chamber at a second end. Each pumping chamber includes a first volume coupled to a pressure inlet, a second volume coupled to a flow inlet and a flow outlet, and a diaphragm separating the first volume from the second volume and deformable such that pressure in the first volume is transferred to the second volume. The diaphragm includes a generally flat membrane separating the pumping chamber into the first volume and the second volume. Each sample tube is located inside the corresponding pumping chamber, the first volume is between the sample tube and outer walls of the pumping chamber, the second volume is internal to the sample tube, and the diaphragm includes the sample tube. Each sample tube is coupled to the flow control subsystem through flow apertures in the pumping chamber, and each of the flow apertures is sized to attenuate pressure changes in the sample fluid such that pressure changes in the sample tube are not communicated to the flow control system. The flow apertures in each pumping chamber include a flow inlet and a flow outlet, one of the flow inlet or the flow outlet of each pumping chamber is sized to attenuate pressure changes in the pumping chamber such that pressure changes in the pumping chamber are not communicated to the flow control system, and the other of the flow inlet or flow outlet of each pumping chamber is sized to communicate pressure changes in the pumping chamber to the sample tube coupled to the pumping chamber.

The pressure control subsystem also includes a first pressure manifold coupled to the first dynamic pump through the mass of pumping fluid, and having a plurality of outlets corresponding to the number of sample tubes in the plurality of sample tubes, a second pressure manifold coupled to the first dynamic pump through the mass of pumping fluid, and having a plurality of outlets corresponding to the number of sample tubes in the plurality of sample tubes, and a plurality of pumping tubes, each pumping tube coupling one of the outlets of the first or second pressure manifolds to one of the pumping chambers. The pressure control subsystem also includes a second dynamic pump, equipped to induce pulsatile pressure in a second portion of the mass of pumping fluid, the first dynamic pump inducing pulsatile pressure in a first portion of the mass of pumping fluid, a first pressure manifold coupled to the first dynamic pump through the first portion of the mass of pumping fluid, and having a plurality of outlets corresponding to the number of sample tubes in the plurality of sample tubes, a second pressure manifold coupled to the second dynamic pump through the second portion of the mass of pumping fluid, and having a plurality of outlets corresponding to the number of sample tubes in the plurality of sample tubes, and a plurality of pumping tubes, each pumping tube coupling one of the outlets of the first or second pressure manifolds to one of the pumping chambers. A first pressure balancing tube is coupled to the pressure control system, a second pressure balancing tube is coupled to the flow control system, and a filter housing couples the first pressure balancing tube to the second pressure balancing tube through a filter.

The flow control subsystem also includes a first flow manifold coupled to an outlet of the mean flow pump and having a plurality of outlets corresponding to the number of sample tubes in the plurality of sample tubes, and a second flow manifold coupled to an inlet of the mean flow pump and having a plurality inlets corresponding to the number of sample tubes in the plurality of sample tubes, each flow loop connecting one outlet of the first flow manifold to one inlet of the second flow manifold and including one of the sample tubes and the corresponding pumping chamber, a first flow tube coupling the outlet of the first flow manifold to a flow inlet in the pumping chamber, a second flow tube coupling a flow outlet in the pumping chamber to the inlet of the second flow manifold. The first flow tube is coupled to the flow inlet in a first pumping chamber, and the second flow tube is coupled to the flow outlet in a second pumping chamber, the two pumping chambers being coupled to first and second ends of the sample tube. Each of the flow loops also conducts the flow of fluid to a filter array. The filter array includes, for each flow loop a first branch dividing the flow loop into a first flow pathway coupled to a first filter housing and a second flow pathway coupled to a second filter housing, a switch selectively opening one of the first or second flow pathways and closing the other of the first or second flow pathways, a second branch coupling the first flow pathway and the second flow pathway to a flow rate sensor. The flow rate sensor of each flow loop is coupled to the switch in the filter array associated with the corresponding flow loop.

In general, in some aspects, a pumping chamber for use with a pressure control system and a flow control system includes a first volume coupled to a pressure inlet, a second volume coupled to a flow inlet and a flow outlet, and a diaphragm separating the first volume from the second volume, pressure in the first volume inducing deformation of the diaphragm to induce pressure in the second volume.

In general, in some aspects, a filter module for use in a flow control system includes a first branch dividing an incoming flow into a first flow pathway coupled to a first filter housing and a second flow pathway coupled to a second filter housing, a switch selectively opening one of the first or second flow pathways and closing the other of the first or second flow pathways between the first branch and the first and second filter housings, a second branch coupling outlets of the first and second filter housings to a flow rate sensor.

Advantages include obtaining accurate particle counting and capture from multiple specimens without mixing of particles between the specimens.

Other features and advantages will be apparent from the description and the claims.

BRIEF DESCRIPTION OF THE DRAWINGS

FIG. 2A shows a side view of a pressure control system for a multi-specimen testing system.

FIG. 2B shows an end view of a pressure control system of FIG. 2A.

FIG. 5A shows a sample tube and two pumping chambers for a single sample.

FIG. 5B shows a connection between the pressure control system of FIG. 2 and the sample fluid system of FIG. 3.

FIG. 6 shows an alternative embodiment of a sample tube and pressure chamber.

DESCRIPTION

Figure 1A:
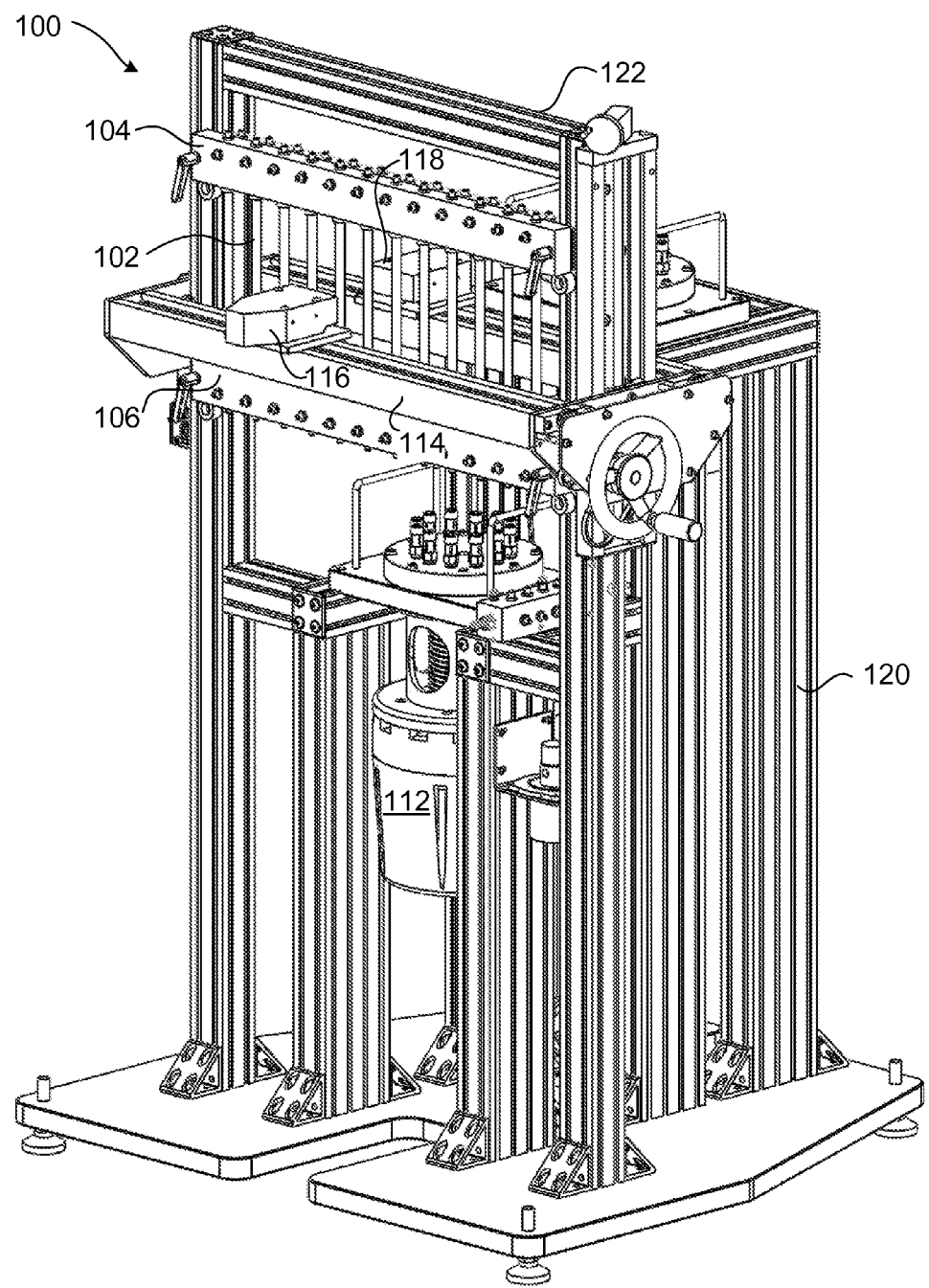
FIG. 1A shows an isometric view of a multi-specimen testing system.
Figure 1B:
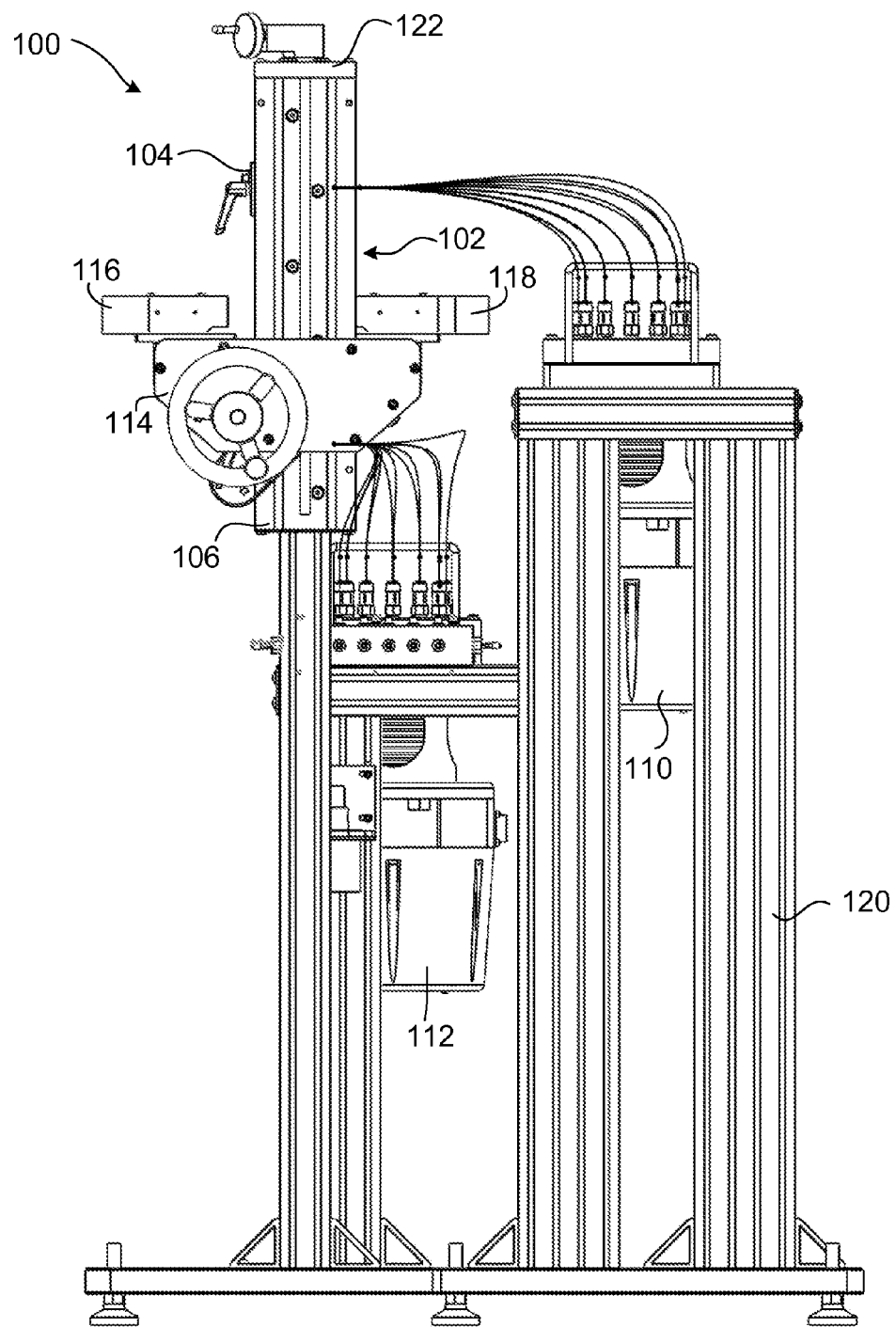
FIG. 1B shows a side view of the multi-specimen testing system of FIG. 1A.

As shown in FIG. 1, a multi-specimen testing system 100 allows an investigator to stimulate a number of samples in parallel. The system of FIG. 1, in particular, is used for testing implantable cardiovascular devices, such as stents or stent/grafts located inside sample tubes 102 that serve as simulated blood vessels, also referred to as mock arteries. Latex has commonly been used for this purpose, but in some examples, such as coated stent durability testing, silicone may be preferred for its particulate shedding properties. In some examples, the sample tubes and supporting structures are sized to accommodate sample devices having inner diameters between around 2 to 14 mm and lengths of around 100 to 200 mm for test simulations of coronary stent/grafts. Other example systems, such as for peripheral vessel simulation, accommodate larger devices. Previous systems, such as the ElectroForce™ 9110 from the ElectroForce Systems Group of Bose Corporation, located in Eden Prairie, Minn., have held twelve (12) specimens in a circular configuration, with the sample tubes held horizontally between two motors, as described in U.S. Pat. No. 5,670,708, noted above. In contrast, in the system shown in FIG. 1, the sample tubes 102 are located vertically and oriented in a common plane. Each of the sample tubes is connected at its ends to upper and lower pumping headers 104 and 106, which are in turn connected to upper and lower dynamic pump motors 110 and 112. A measurement platform 114 positions measurement instruments 116, 118 near the sample tubes and allows a user to control the position of the instruments. Other support structures 120, 122 hold the above components in position in a conventional manner.

The dynamic pump motors 110 and 112 are part of a pressure control system 200, shown in FIG. 2, that generates a cyclic pressure profile in the sample tubes by raising the pressure of the fluid in the system. In some examples, the pressure control system is designed to stimulate the sample devices to induce an radial inner diameter strain of around 3 to 5 percent at frequencies of 1 to 150 Hz. In the pressure control system 200, each of the dynamic pump motors 110 and 112 applies pressure in a corresponding upper and lower fluid volume 202, 204. Upper and lower dynamic pump manifolds 206, 208 divide the fluid volumes 202, 204 into separate upper and lower pressure tubes 210, 212 for each sample tube 102. Note that while the pressure tubes 210, 212 are shown as thin lines in the figures, they may be any diameter appropriate to the volume and pressure of the fluids used. The upper and lower pressure tubes are coupled to the upper and lower pumping headers 104 and 106. Each of the pressure tubes, sample tubes, and pumping headers is repeated as many times as there are samples to be tested. In FIG. 2, for clarity, only two of each are shown, and only one of each is labeled. Pressure applied by the dynamic pump motors is transmitted through the fluid volumes, manifolds, pressure tubes, and pumping headers into the sample tubes 102. In some examples, each of the upper pressure tubes 210 is the same length, and each of the lower pressure tubes 212 is the same length, so that the same pressures are applied at the end of each upper or lower tube. When the upper and lower tubes are also the same length as each other, then the same pressure can be applied at each of the upper and lower fluid volumes to apply the same pressures at the upper and lower pumping headers. If the upper and lower tubes are different, then different forces may be applied at the upper and lower fluid volumes to assure that the same pressures are applied at the upper and lower pumping headers. When the same pressure is applied in both pumping headers at the same time, the pressure in the sample tube 102 is the same at both ends, controlling the total pressure without creating a net flow. Such a pressure control system is described in U.S. Pat. No. 5,670,708, noted above. Similar techniques are used in the vertical/planar system shown in FIG. 1 to those of the horizontal/circular system of that patent. A dynamic pump 213a includes the dynamic pump motor 112 and the dynamic pump manifold 208. A dynamic pump 213b includes the dynamic pump motor 110 and the dynamic pump manifold 206. One advantage of pressurizing the sample tubes from both ends is that the effective length of each sample tube, as viewed from a pressure source at one end, is cut in half, allowing higher-frequency testing with more uniform strain distribution over the length of the sample tube. Another advantage is that each dynamic pump 213a, 213b must move half as much fluid to achieve a given pressure, allowing greater operating frequencies.

Figure 3:
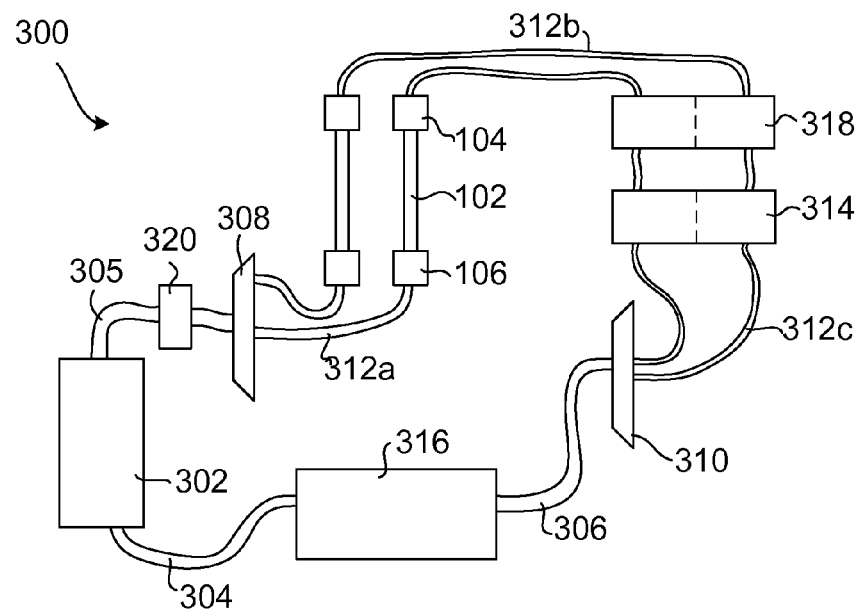
FIG. 3 shows a schematic view of a sample fluid system for a multi-specimen testing system with separate flow loops.

As shown in FIG. 3, a sample fluid system 300 is connected to the sample tubes 102 and pumps a sample fluid through the sample tubes for transport and analysis of particles shed by the devices under test in the sample tubes. Pumping a sample fluid through the tubes also allows control of environmental factors, such as temperature or pH, to be conducted remotely from the sample. The fluid flow is primarily a constant flow. The sample fluid system includes a mean flow pump 302, primary tubing 304, 305, and 306, upstream and downstream sample fluid manifolds 308 and 310, sample fluid tubing 312, a filter array 314, and a sample fluid reservoir 316. The mean flow pump 302 receives fluid from the reservoir 316 through primary supply tubing 304 and pumps it into the system through the primary delivery tubing 305. At the upstream manifold 308, the fluid is divided into as many sample fluid tubes 312a as there are sample tubes 102. We sometimes refer to the individual pathways created by the sample fluid tubes as sample fluid loops. The sample fluid tubes 312a deliver the sample fluid to the lower pumping headers 106, from which it flows through the sample tubes 102 and into the upper pumping headers 104. In some examples, flowing the sample fluid upward through the sample tubes 102 assists in purging of air from the fluid, discussed below. In some examples, the fluid flows in the other direction, so accommodating particles that are dense enough to fall downward, against an upward flow. The sample tubes do not have to be oriented vertically, as shown, but may also be located horizontally or at any arbitrary angle desired by the user. Description of the components as "upper" and "lower" is for reference only. Leaving the upper pumping header 104, additional sample tubing 312b takes the sample fluid to the filter array 314, where any particulate now in the sample fluid is filtered out, as described in more detail below, before the separate sample fluid loops in tubing 312c rejoin at the downstream manifold 310. The primary return tubing 306 returns the sample fluid to the reservoir 316. In some examples, the individual sections of sample tubing 312 making up each sample flow loop are the same length, within each step of the pathway, to assure uniform flow and mean pressure in each of the sample flow loops. One of skill in the art will appreciate that the systems shown in FIGS. 2 and 3 can be used together to provide both pressure and flow control in the sample tubes 102.

The sample fluid system 300 shown in FIG. 3 also includes an optional in-line particulate measurement system 318 for counting and/or measuring particles in the sample fluid. The particulate measurement system 318 includes light-obscuration particle counters that measure the number and, in some cases, size of the particles passing through each flow loop. In some examples, the sample fluid system includes a filter 320 between the mean flow pump 302 and the upstream manifold 308 to capture any particulate shed by the mean flow pump 302 so that it does not contaminate the fluid flowing through the sample tubing 312.

Fluid Segregation

When multiple samples are to be tested and particulate shed from the samples is to be monitored, it is desirable to keep the particles shed from the samples separated, so that each sample can be measured individually. The systems shown in FIGS. 1, 2, and 3 apply a common pressure and a common fluid flow to all the samples, while maintaining segregation between the flow loops so that the particles shed from each sample can be measured or captured without mixing.

Figure 4:
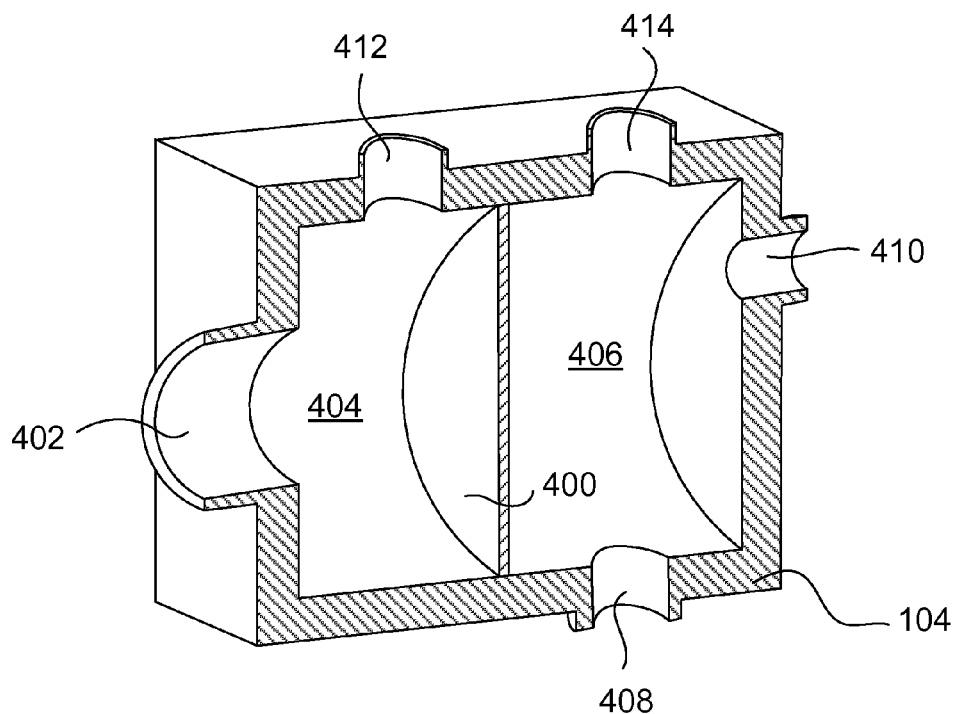
FIG. 4 shows a pumping chamber for a single sample.

There are two separate areas of segregation. First, as shown in FIGS. 4 and 5, the pumping fluid that is used to drive pulsatile stimulation of the samples is isolated from the fluid that flows through the samples and transports any shed particles. This prevents any stray particles or bubbles from the pulsatile pumping system from entering the sample flow loops or vice versa. It also prevents particles shed by one sample from entering the flow loop of another sample through the pumping fluid. This isolation is designed such that there is no fluidic communication, but enables the transfer of pulsatile/dynamic pressure from the dynamic pumps to the flow loops. Second, as shown in FIG. 3, the fluid that flows through the samples is driven by a common mean flow pump but divided by the upstream sample fluid manifold into separate loops for each sample. The sample fluid flowing through each sample flow loop is passed through particle counting systems, if used, and then through individual particle filters. After the sample fluid is filtered, the flow paths rejoin at the downstream sample fluid manifold and are returned to the sample fluid reservoir. By filtering the flow loops individually, any particles that are shed are associated with the sample they originated from, while a single fluid reservoir and mean flow pump can be used to drive the sample fluid through all the samples. In some examples, a pathway exists for shed particles to move upstream to the first sample fluid manifold, where they could mix. In such a system, additional upstream filters can be used in each flow loop to maintain segregation of the flow loops. Alternatively, separate flow pumps could be used to provide entirely segregated flow loops.

FIG. 4 shows a cross-section of one of the pumping headers 104 from FIGS. 1, 2, and 3. Inside the chamber, a diaphragm 400 separates pumping fluid, on the left, from sample fluid, on the right. A pressure fluid port 402 admits dynamic pumping fluid from the pressure control system 200 (not shown). This controls the pressure in a left chamber 404 of the pumping header 104. If the pressure in the left chamber 404 is raised or lowered relative to the pressure in a right chamber 406, the diaphragm 400 flexes to equalize the pressure in the left and right chambers. When the pressure in the left chamber is higher than that on the right, the diaphragm moves to the right, increasing the pressure in the right chamber 406. When the pressure in the left chamber is lower than that on the right, the diaphragm moves to the left, decreasing the pressure in the right chamber 406. The right chamber is coupled to the sample tube 102 (not shown) through a sample fluid inlet port 408. Sample fluid leaves through a sample fluid outlet port 410. When the pressure in the right chamber is raised or lowered by action of the diaphragm, that pressure is communicated to the sample tube through the sample fluid shared between the right chamber and the sample tube. This allows pressure from the pressure control system 200 to be transferred to the sample fluid system 300 without mixing of the fluids or any transfer of particulates. The lower pumping header 106 is constructed and connected similarly to the upper pumping header, such that pressure is controlled at both ends of the sample tube, as shown in more detail in FIG. 5. In some examples, the diaphragm is designed with an area and stroke to displace the fluid volume required to extend the sample tube radius along the effective length of the tube. It is preferable for the diaphragm to have sufficient compliance and durability to yield effective linear pressure transfer over the duration of many tests. In some examples, one test typically involves 400 million cycles to perform a 10 year simulation.

The sample fluid tubing 312 (not shown) will be coupled to the right chamber 406 at the outlet port 410, to accommodate the flow of fluid from the sample tube on through the sample flow loop, but in some examples, this connection is made through a small aperture that does not efficiently transmit rapid changes in pressure, so the fluid pressure in the flow loops outside of the pumping headers and sample tube remains relatively constant and the dynamic pressure changes are maximized in the sample tube region. Access ports 412 and 414 allow various functions, such as bleeding gasses from the right and left chambers, or inserting probes or materials into the fluid loops, as described below.

FIG. 5A shows a matched pair of upper and lower pumping headers 104 and 106 with a sample tube in-between and pumping and sample fluid tubing attached. A sample device 500 is located in the sample tube 102. Like the upper pumping header 104, the lower pumping header 106 includes left and right chambers 424 and 426 separated by a diaphragm 420, and pressure inlet 422. The roles of sample fluid ports 428 and 430 are reversed relative to corresponding ports 408 and 410 in the upper chamber, as sample fluid flows in through port 430 and out, to the sample tube 102, through port 428. Access ports 432 and 434 function similarly to ports 412 and 414. In operation, the dynamic pressure control system applies pressure simultaneously to the two left chambers 404 and 424 through tubing 210 and 212. Through the diaphragms 400 and 410, this creates a uniform pressure in the right chambers 406 and 426, thereby transmitting the pressure to the sample tubes simultaneously from both ends and applying internal radial pressure to the sample device 500. While the sample tubes are shown directly connected to protrusions from the pumping headers, in implementation various types of fittings may be used depending on the nature of the sample tubes and the types of fluid in use. Sample fluid flows into the right chamber 426 of the lower pumping header 106 from the sample tubing 312a, upward through the sample tube 102 to the right chamber 406 of the upper pumping header 106, and out through the sample tubing 312b.

In some examples, to avoid applying a long-term bias on the membrane, the mean pressures on the two sides of the membrane are kept balanced. In the example of FIG. 5B, pressure balancing tubing 440 connects the bulk fluid in the pressure system 200 and the sample fluid system 300 through a filter 442. The plumbing 440 and filter 442 are sized to balance pressures while minimizing net flow of fluids between the two systems. This keeps the mean pressures equalized, with little effect on the dynamic performance within the sample tubes 102. The filter 442 maintains cleanliness of the sample fluid.

In some examples, the diaphragms 400, 420 are actuated by a structural force source, rather than through fluid. For example, a motor may directly press on the diaphragms, or may do so through a mechanical linkage. Using a mechanical actuator rather than pumping fluid may simplify the pumping side of the system, removing the need to manage the pumping fluid. FIG. 6 shows an alternative embodiment for segregating the pump fluid. In this example, the sample tube 102 is located within a chamber 502 filled with the pump fluid. The pump fluid in the chamber 502 is driven by the pulsatile pumping system (not shown) and applies pressure to the exterior of the sample tube, thereby applying external radial pressure to the sample device 500. The sample tube itself maintains the separation between the pump fluid and the sample fluid, which flows through the sample tube as before. In some examples, the sample tube is located upstream or downstream of the concentric tubes shown in FIG. 5, and when pressure is applied to the inner tube, fluid is pumped into our out of that tube, and thereby out of or into the sample tube.

Direct Pressure Monitoring and Control

Figure 7:
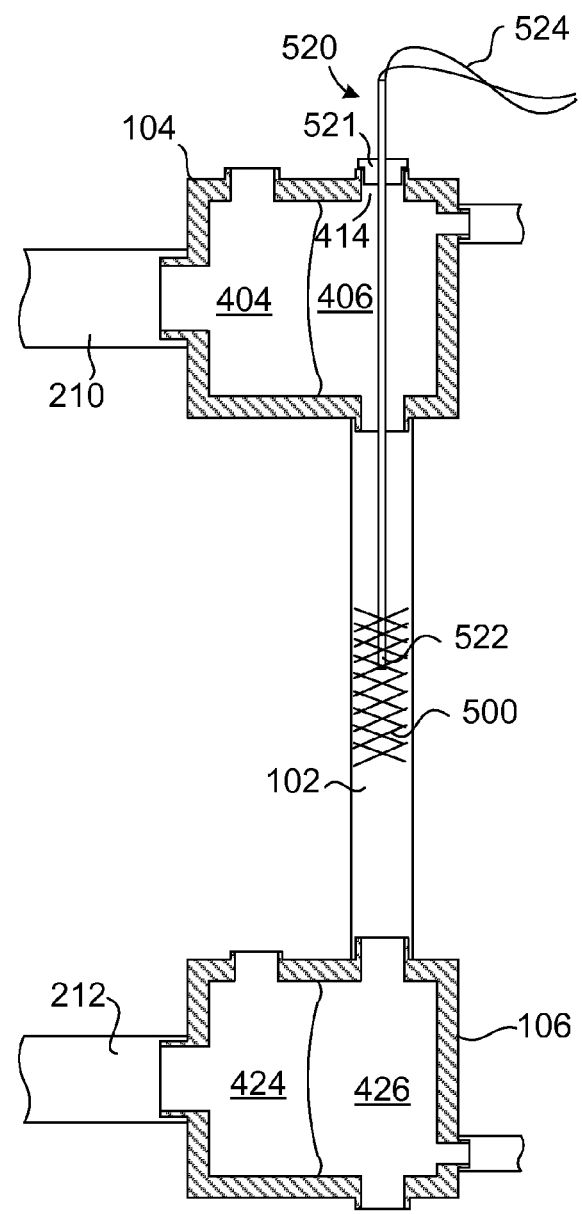
FIG. 7 shows a pressure sensor located within a sample tube.

In some examples, control of the system is improved by providing direct measurement of the pressure in the sample tube, as compared to, for example, monitoring the pressure remotely from the sample and inferring the true sample pressure. FIG. 7 shows one design for directly measuring the pressure in the sample tube. In this example, a catheter-type probe 520 is inserted through a sealing fitting 521 in the access port 414 in the upper pumping header 104 and into the sample tube 102. A sensor 522 at the tip of the probe 520 is located at the mid-point of the sample tube or other location of interest, based on the sample device 500 being tested. Sensor leads 524 are connected to whatever monitoring and control system is in use, or to intervening electronics to convert readings of the sensor to usable signals. In some examples, a T-joint is provided within the sample tube to provide direct access for the pressure sensor to the sample tube. The pumping headers with separation diaphragm from FIGS. 4 and 5 are used for illustration in FIG. 7, but the technique of FIG. 7 is generally applicable to any pumping strategy. In some examples, when diaphragms are utilized, the pressure sensor may be located in either of the pumping chambers (404 or 406, 424 or 426) to isolate the sensor from the flow loop while effectively measuring the dynamic pressure at the tube inlet.

If the pressure control system is an enclosed system, pressure measured at the sample may be used as a direct feedback signal in the control loop. In an open-to-atmosphere pressure control system, the sample pressure may be used in a mixed mode-controller where the pressure is a feedback signal for a dynamic controller and the displacement of the powerheads is a feedback signal for the mean controller. This controller and sensor configuration enables a higher performing direct controller on pressure amplitude. This has the advantages of reducing the additional dynamics present in direct displacement control that often limit controller bandwidth and reducing the effects of changing test system characteristics over the duration of a long-term fatigue test. This additional bandwidth and direct control enables improved testing at higher frequency with higher pressure waveform fidelity of the sample pressure signal over the extended duration of a test. In either situation, control of the pressure is advantageously improved over removed pressure measurement solutions. This is especially valuable in systems where the pressure is varied at high frequencies, where pressure values can vary significantly and dynamically throughout the system.

Non-Disruptive Filter Switching

Figure 8:
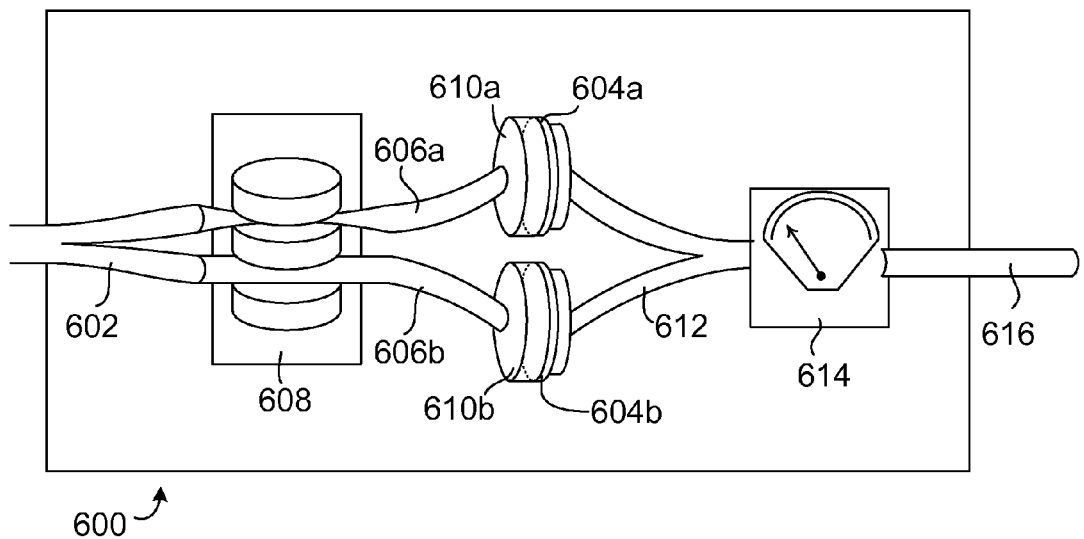
FIG. 8 shows a switching and filtering system.

As mentioned above, in some applications, filters are used to capture particles shed within each flow loop before the flow loops rejoin in the second sample fluid manifold. Such filters may eventually become sufficiently full of particles that they obstruct the flow and need to be changed. In addition, in some applications, it is desirable to remove the filters for analysis of the captured particles while the test continues. In addition to the number and size of the particles, which may also be determined by in-line particle counters, filters allow the investigator to observe the makeup of the captured particles. Based on the particulate makeup, the investigator might infer the source and biocompatibility of the particulate to evaluate its impact. FIG. 8 shows a filter switching system 600 that allows filters to be changed without disrupting the test. In some examples, such a filter switching system is used in the filter array 314 of FIG. 3.

In the example of FIG. 8, the sample fluid tubing 602 branches and flows through two filters 604a, 604b. The tubing in FIG. 8 represents only one sample fluid flow loop—the same system 600 will be repeated for each flow loop in a multiple-sample system. After branching, two sections of sample fluid tubing 606a and 606b pass through a switching valve 608. In some examples, the switching valve 608 is a solenoid pinch valve, which is a non-invasive valve that is less likely to cause particulate shedding itself than more invasive valves. The switching valve 608 selectively closes one of the tubes passing through it and leaves the other open. Each of the tubing sections 606a and 606b ends at a filter holder 610a, 610b. After the filters, a new tubing section 612 rejoins the two pathways and enters a flow meter 614, which may be an impeller-style flow meter or any other in-line flow measurement device. After the flow meter the final section of tubing 616 leaves the filter system 600 and continues in the main sample fluid loop, i.e., becoming the final section on sample tubing 312c in FIG. 3.

Whenever the active filter, e.g., filter 604b in FIG. 8, needs to be changed, the switching valve 608 opens the currently-closed tubing (606a) and closes the currently-open tubing (606b). This cuts off sample fluid through the filter to be changed, and begins flowing sample fluid through the other filter (604a). The now-inactive filter is then removed and replaced. In some examples, a quick-disconnect fitting is used to attach the filters, effectively shutting off the tubing and avoiding back flow when the filter is removed. In some examples, other measures are used, such as one-way flow valves or a second switching valve downstream of the filters. While we illustrate two filters, any number of filters may be used with an appropriate switching arrangement, depending on the timing needs of the study and the, allowing the manual filter replacement to be less frequent.

In some examples, the switching valve 608 is triggered automatically based on a detected need to change the filters. As the active filter collects particles from the sample fluid, it begins to restrict flow through the active side of the filter system. The flow meter measures the flow through the system, thus the control system (not shown) will detect when the flow is restricted to the point that the filter needs to be changed. When a threshold flow condition or other parameter is met, the control system will trigger the switching valve 608 to change which path is open, and will alert the operator or an automated filter switching system to change filters in the now-inactive path. In addition to the mean or instantaneous flow through the system, other parameters that may trigger a filter switch include cycle count in the test system, elapsed time, or total flow volume since the last filter change or over some other time period. In a system with a separate flow pump for each loop, the pressure across the filter may also be a useful measure of whether a filter needs to be changed. A user may program any combination of these parameters, or may use fully manual control and change the filter when desired by manually triggering the switching valve 608. FIG. 8 shows the flow meter downstream of the filters. In general, the flow meter may be located anywhere along the flow path, but locating it downstream of the filters avoids particulate shed by the flow meter itself contaminating the sample.

Gas Management

Fatigue testing systems for stents typically rely on an incompressible fluid for transmitting pressure pulses from a dynamic pump to a flexible tube, which contains the stent. These pulses cause radial distention in this tube, as well as the stent implanted within it, typically at an accelerated rate (>40 Hz) when compared to the physiologic rate (~1.2 Hz). Any compressible gasses within the system attenuate these pressure waves, reducing the efficiency of the system, which lowers either the testing frequency (increases test duration), or the achievable distention levels. In addition, it is advantageous to remove dissolved gasses from the sample fluid when particulate counters are in use, as any bubbles that form in the sample fluid may be mistaken for particles. Several approaches may be combined to limit the amount of dissolved gasses and avoid gasses coming out of solution to form bubbles.

Figure 9:
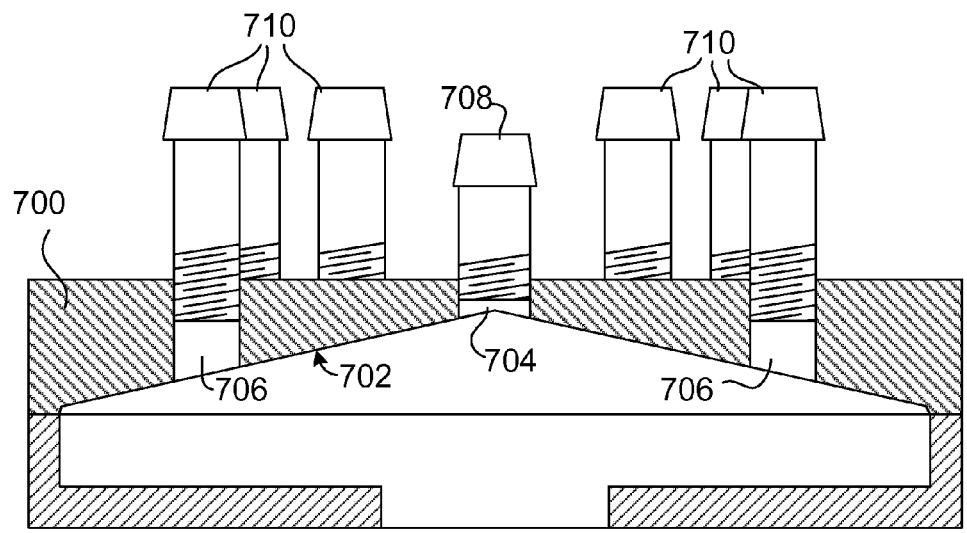
FIG. 9 shows a pump fluid manifold.

FIG. 9 shows a cross-sectional view of a manifold 700 for use in the pressure control system of FIG. 2 (e.g., manifolds 206 and 208). A conical internal profile 702 leads up to a central degassing bleed port 704. This profile 702 encourages any bubbles in the main bulk of the pressure fluid to rise to the bleed port 704 rather than exiting through the other ports 706 into the pumping fluid tubes that lead to the pumping headers 104 and 106 (see, e.g., FIGS. 1 and 2). Connectors 708, 710 are shown for reference only—any appropriate method of connecting valves or tubing to the manifold ports 704 and 706 may be used.

Access ports 412, 414, and 432 for both the pressure fluid side and the sample side of the system are shown in the pumping headers 104 and 106 in FIG. 5A. By using these access ports located at the highest points in the sample fluid flow loops (see FIG. 1) and pressure system (see FIG. 2) as bleed ports, gasses coming out of solution in the sample fluid and any bubbles getting or originating past the manifold bleed port 704 in the pressure fluid will rise to the bleed ports in the pumping headers, and the system will not have to be moved around or otherwise disturbed to get the gasses to the bleed ports.

Given the use of flexible tubing which is typically gas permeable to at least some extent, it may be necessary to continuously or periodically remove gas from the system, as opposed to simply doing it once during system setup. In some examples, a fluid degassing system is used to remove gasses at a controlled point and keep the total level of dissolved gasses low enough that the gasses will remain in solution in the rest of the system, including any of the various points where changes in pressure and temperature might encourage gasses to come out of solution. In some examples, tubing with high gas permeability is combined with a differential pressure, such as by locating it at a high pressure position relative to the environment and/or by pulling a vacuum on the outside of the tubing. Commercially available in-line degassing equipment may also be used. One example is the Liqui-Cel® line of membrane contactor from Membrana-Charlotte, a division of Celgard, LLC, located in Charlotte, N.C. In membrane degassing systems, the fluid to be degassed separated from a vacuum by a semi-permeable membrane through which dissolved cases are pulled by the vacuum. In some examples, the membrane forms tubes passing through the fluid, with the vacuum presented in the tubes. In some examples, this is reversed, with the fluid passing through membranous tubes that are located within a chamber under vacuum.

Strobe Illumination of Sample Tubes

Figure 10:
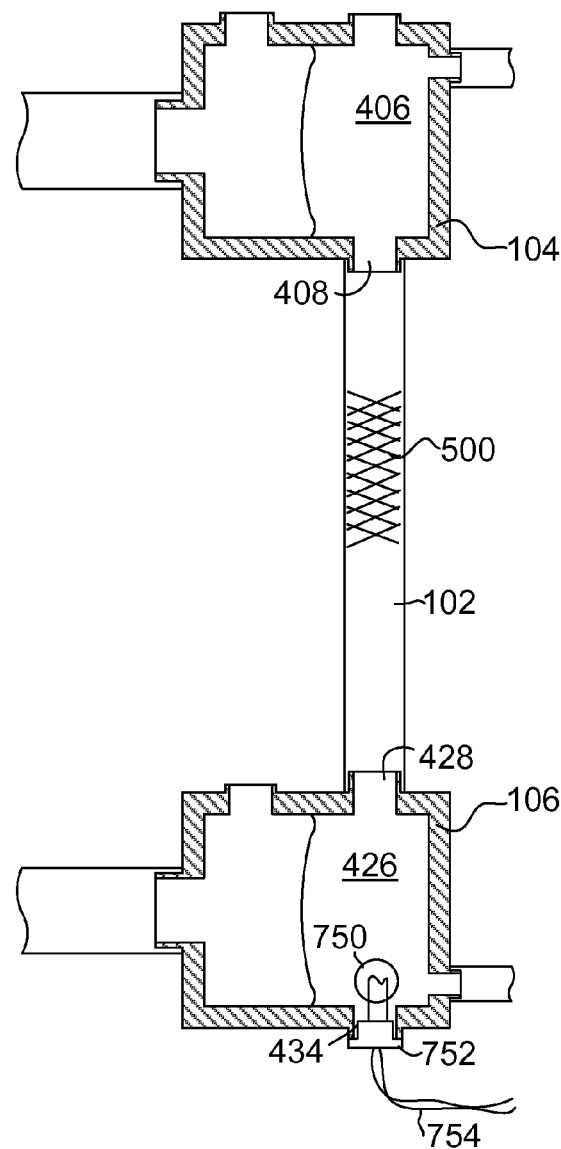
FIG. 10 shows a light source located within a pumping chamber.

In some applications, the rates at which the samples are stimulated exceed the ability of a human observer to see changes in the device under test. One common solution to such a situation is to illuminate the sample with a strobe light, tuned to provide a static image of the sample (if the strobe frequency is an integral fraction of the stimulation frequency) or a slowly evolving image (if the strobe frequency is near an integral fraction of the simulation frequency). With such an image, the observer may be able to see movement of the sample that was not apparent at its true cycle speed. As shown in FIG. 10, one way to provide such illumination is to locate an LED or other small strobe light within one anchor of the sample tube. In particular, in FIG. 10, an LED 750 is located in the lower pumping header 106, seated in the lower sample fluid access port 434 with a plug 752. Lead lines 754 control the LED. By connecting the light source to the same controller (not shown) as the pressure source, the frequency of the strobe can be automatically tuned to provide a steady or slowly evolving image of the sample. Tying the strobe to the controller has advantages over a manually controlled strobe, including eliminating user-to-user variability and providing a consistent light pattern to each sample in the system and throughout the duration of the test. Due to internal reflection at the fluid-surface interfaces, the light from such a source will travel through the sample fluid and illuminate the device 500 under test without significant leakage of light through the rest of the sample tube 102.

Multiple-Plane Sample Tube Measurement

Figure 11:
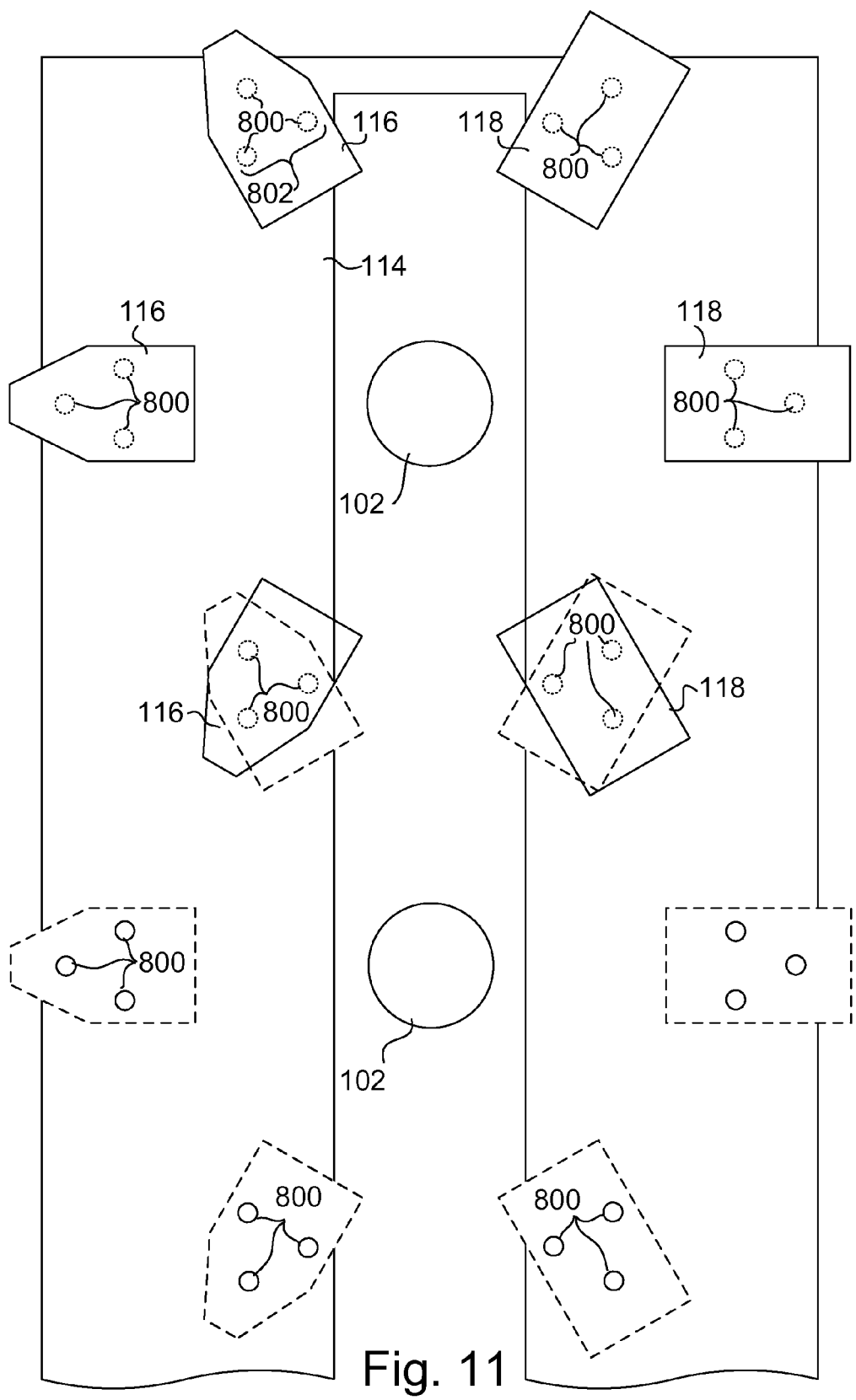
FIGS. 11 and 12 show mounting arrangements for instrumentation
Figure 12:
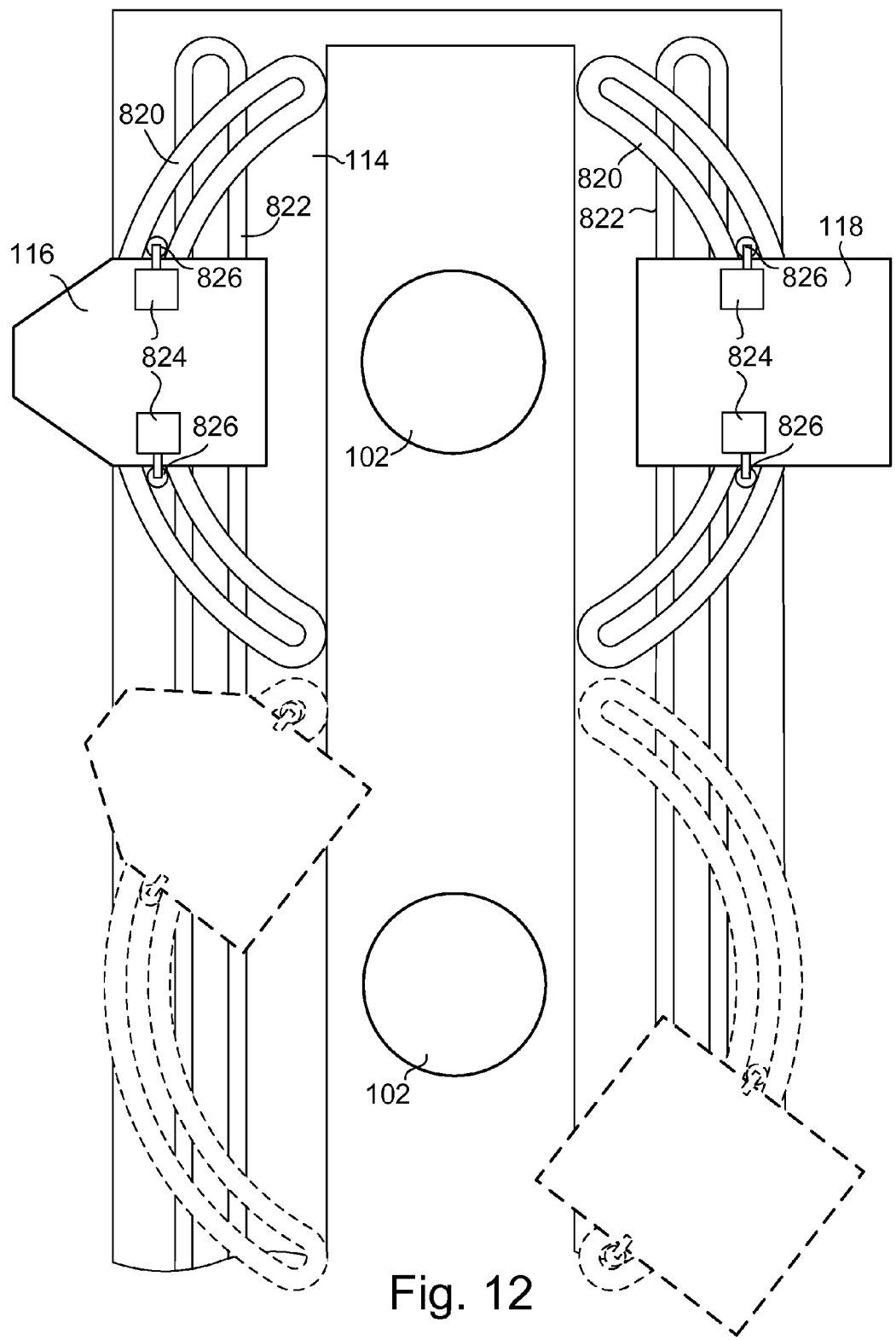

In the system shown in FIG. 1, an optical emitter 116 and detector 118 move laterally along the measurement platform 114, moving among the line of sample tubes 102 to measure the diameter of each sample tube in turn. The platform 114 can also move up and down along the length of the sample tubes, positioning the emitter 116 and detector 118 to measure the diameter of each sample tube at multiple points. As shown in FIG. 1, the emitter and detector only measure in a single direction, measuring the tube diameter perpendicular to that direction at whatever position they are moved to. In some applications, it is desirable to measure the diameter along different directions, i.e., providing the cross-sectional width of the tube in different planes. This is useful, for example, for identifying non-symmetric failures of the devices under test. FIGS. 11-13 show several different embodiments for providing these measurements.

In some examples, as shown in FIG. 1, mounting holes 800 are located in the measurement platform 114 at various angles around each sample tube. The emitter 116 and detector 118 may be located at any matched set 802 of mounting holes 800 to be accurately positioned to measure the sample tube. In the example of FIG. 11, the sets of mounting holes are positioned at 60 degree angles along a circular path, so that the emitter and detector will be positioned the same distance from the sample tube in each position. Alternatively, the mounting holes may be located at differing distances. For example, the mounting holes may all be located in a single line. This would allow narrower measurement platform, but would require the measurements to be adjusted for the differing distances involved from each position. Other angles may also be used. In the example of FIG. 1, the mounting holes are configured to allow some of the mounting holes to be used for multiple samples, by locating the emitter and detector on the same holes but in different directions. In the example of FIG. 1, three pairs of emitters and detectors are shown around one sample tube, with alternative positions of one of the pairs shown in broken lines. If the detectors and emitters are indeed small enough to occupy multiple positions without interfering with each other, several may be used to produce multiple measurements simultaneously. Alternatively, one set may be repositioned between each of the positions as desired.

In some examples, as shown in FIG. 12, a first track 820 is provided along which the emitter 116 and detector 118 may be repositioned, while the first track itself moves along a second track 822 to reach multiple sample tubes 102. The curved track shown is merely one example—other configurations, such as a single straight track, may be used, if the emitter and detector can pivot as needed to face the sample tube. In addition to allowing a greater number of measurement angles, the continuous tracks, however implemented, allow the repositioning of the emitter and detector to be automated, for example by motors 824 and wheels 826. The vertical movement of the measurement platform (see FIG. 1) may also be controlled by a motor and thereby automated.

Other implementations are within the scope of the following claims and other claims to which the applicant may be entitled.

What is claimed is:

1. A system comprising:
   a plurality of first pumping chambers;
   a plurality of sample tubes;
   a plurality of flow loops, wherein each sample tube is coupled to a corresponding one of the first pumping chambers to define at least a portion of a respective flow loop;
   a pressure control subsystem comprising a first dynamic pump, equipped to induce pulsatile pressure in a mass of pumping fluid coupled to the pumping chambers; and
   a flow control subsystem comprising a mean flow pump equipped to generate a flow of sample fluid in a the plurality of flow loops, each of the flow loops conducting the flow of sample fluid between the mean flow pump and one of the sample tubes;
   each pumping chamber coupling pressure from the pumping fluid to the sample fluid.

2. The system of claim 1, further comprising a plurality of second pumping chambers, wherein each sample tube is coupled to one of the first pumping chambers at a first end of that sample tube and is coupled to a second pumping chamber at a second end of that sample tube.

3. The system of claim 1 wherein each pumping chamber includes a diaphragm, a pressure inlet, a flow inlet, and a flow outlet, and defines
   a first volume coupled to the pressure inlet and
   a second volume coupled to the flow inlet and the flow outlet,
   the diaphragm separating the first volume from the second volume and being deformable such that pressure in the first volume is transferred to the second volume.

4. The system of claim 3 wherein:
   the diaphragm comprises a generally flat membrane separating the pumping chamber into the first volume and the second volume.

5. The system of claim 3 wherein:
   each sample tube is located inside the corresponding pumping chamber,
   the first volume is between the sample tube and outer walls of the pumping chamber,
   the second volume is internal to the sample tube, and
   the diaphragm comprises the sample tube.

6. The system of claim 1 wherein:
   each sample tube is coupled to the flow control subsystem through flow apertures in the pumping chamber.

7. The system of claim 6 wherein:
   the flow apertures in each pumping chamber comprise a flow inlet and a flow outlet.

8. The system of claim 1 wherein the pressure control subsystem further comprises:
   a first pressure manifold coupled to the first dynamic pump through the mass of pumping fluid, and having a plurality of outlets corresponding to the number of sample tubes in the plurality of sample tubes;
   a second pressure manifold coupled to the first dynamic pump through the mass of pumping fluid, and having a plurality of outlets corresponding to the number of sample tubes in the plurality of sample tubes; and
   a plurality of pumping tubes, each pumping tube coupling one of the outlets of the first or second pressure manifolds to one of the pumping chambers.

9. The system of claim 1 wherein the pressure control subsystem further comprises:
   a second dynamic pump, equipped to induce pulsatile pressure in a second portion of the mass of pumping fluid, the first dynamic pump inducing pulsatile pressure in a first portion of the mass of pumping fluid;
   a first pressure manifold coupled to the first dynamic pump through the first portion of the mass of pumping fluid, and having a plurality of outlets corresponding to the number of sample tubes in the plurality of sample tubes;
   a second pressure manifold coupled to the second dynamic pump through the second portion of the mass of pumping fluid, and having a plurality of outlets corresponding to the number of sample tubes in the plurality of sample tubes; and
   a plurality of pumping tubes, each pumping tube coupling one of the outlets of the first or second pressure manifolds to one of the pumping chambers.

10. The system of claim 1 further comprising:
    a first pressure balancing tube coupled to the pressure control subsystem;
    a second pressure balancing tube coupled to the flow control subsystem; and
    a filter housing coupling the first pressure balancing tube to the second pressure balancing tube through a filter.

11. The system of claim 1 wherein the flow control subsystem further comprises:
- a first flow manifold coupled to an outlet of the mean flow pump and having a plurality of outlets corresponding to the number of sample tubes in the plurality of sample tubes; and
- a second flow manifold coupled to an inlet of the mean flow pump and having a plurality inlets corresponding to the number of sample tubes in the plurality of sample tubes;
- each flow loop connecting one outlet of the first flow manifold to one inlet of the second flow manifold and comprising:
- one of the sample tubes and the corresponding pumping chamber,
- a first flow tube coupling the outlet of the first flow manifold to a flow inlet in the pumping chamber,
- a second flow tube coupling a flow outlet in the pumping chamber to the inlet of the second flow manifold.

12. The system of claim 11 wherein:
- the first flow tube is coupled to the flow inlet in a first pumping chamber, and
- the second flow tube is coupled to the flow outlet in a second pumping chamber,
- the two pumping chambers being coupled to first and second ends of the sample tube.

13. The system of claim 1, further including a filter array, wherein
- each of the flow loops further conducts the flow of sample fluid to the filter array.

14. The system of claim 13 wherein the filter array comprises, for each flow loop:
- first and second filter housings, a first branch dividing the flow loop into a first flow pathway coupled to the first filter housing and a second flow pathway coupled to the second filter housing;
- a switch selectively opening one of the first or second flow pathways and closing the other of the first or second flow pathways; and
- a flow rate sensor, a second branch coupling the first flow pathway and the second flow pathway to the flow rate sensor.

15. The system of claim 14 wherein the flow rate sensor of each flow loop is coupled to the switch in the filter array associated with the corresponding flow loop.

16. A method of controlling dynamic pressure and mean flow in a system comprising: a plurality of sample tubes; a plurality of flow loops, wherein each sample tube is coupled to a corresponding one of a plurality of pumping chambers to define at least a portion of a respective flow loop, the method comprising:

- at a dynamic pump, inducing pulsatile pressure in a mass of pumping fluid;
- coupling the mass of pumping fluid to each of the pumping chambers;
- at a mean flow pump, generating a flow of sample fluid in the plurality of flow loops; coupling pressure from the pumping fluid to the sample fluid; and
- within each of the flow loops, conducting the flow of sample fluid between the mean flow pump and one of the sample tubes.

17. The method of claim 16 wherein coupling the pressure from the pumping fluid to the sample fluid comprises deforming a diaphragm separating the pumping fluid from the sample fluid within the pumping chamber.

18. The method of claim 16 wherein conducting the flow of fluid within each flow loop includes conducting the fluid through a first pumping chamber, through the one of the sample tubes coupled to the first pumping chamber at a first end of the sample tube, and through a second pumping chamber coupled to the sample tube at a second end of the sample tube.

19. The method of claim 16 wherein conducting the flow of sample fluid within each flow loop includes attenuating pressure changes in the sample fluid such that pressure changes in the sample tube are not communicated to another portion of the flow loop.

20. The method of claim 16 wherein:
- inducing pulsatile pressure in the mass of pumping fluid comprises pumping a first portion of the mass of pumping fluid with a first dynamic pump, and pumping a second portion of the mass of pumping fluid with a second dynamic pump; and
- coupling the mass of pumping fluid to each of the pumping chambers comprises:
- separating the first portion of the mass of pumping fluid in a first pressure manifold,
- coupling outlets of the first pressure manifold to each of the pumping chambers,
- separating the second portion of the mass of pumping fluid in a second pressure manifold, and
- coupling outlets of the second pressure manifold to each of the pumping chambers.

21. The method of claim 16 wherein generating the flow of sample fluid in the plurality of flow loops comprises:
- generating a flow in a bulk volume of the sample fluid;
- separating the bulk volume of the sample fluid in a first manifold into the plurality of flow loops; and
- recombining the sample fluid from the plurality of flow loops in a second manifold into the bulk volume of the sample fluid.

* * * * *